United States Patent [19]

Mui

[11] Patent Number: 5,250,716

[45] Date of Patent: Oct. 5, 1993

[54] METHOD FOR MAKING A SILICON/COPPER CONTACT MASS SUITABLE FOR DIRECT REACTION

[76] Inventor: Jeffrey Y. P. Mui, 21 Rita La., Bellingham, Mass. 02019

[21] Appl. No.: 889,423

[22] Filed: May 28, 1992

[51] Int. Cl.$^5$ .............................................. C07F 7/04
[52] U.S. Cl. ............................. 556/472; 252/182.32; 502/243
[58] Field of Search ................... 556/472; 252/182.32; 502/232, 240, 243

[56] References Cited

U.S. PATENT DOCUMENTS

| | | | |
|---|---|---|---|
| 4,314,908 | 2/1982 | Downing et al. | 556/472 X |
| 4,645,851 | 2/1987 | Prud'Homme | 556/472 |
| 4,762,940 | 8/1988 | Halm et al. | 556/472 |
| 5,015,751 | 5/1991 | Feldner et al. | 556/472 |

*Primary Examiner*—Arthur C. Prescott
*Attorney, Agent, or Firm*—William Nitkin

[57] ABSTRACT

A method of preparing an active silicon/copper contact mass for the direct reaction of organic halides with silicon to make organohalosilanes by contacting a particle size distribution of silicon with a copper catalyst vapor, aerosol or a combination of vapor and aerosol. The copper catalyst aerosol can be produced by rapid nucleation of the vapor, by an exothermic reaction between copper metal and chlorine gas or by ultrasonic energy dispersion of a solution of a copper compound to a fine mist consisting of extremely fine particles 0.1 to 0.01 micron or smaller. The preferred copper catalyst is copper chloride. The small, sub-micron size copper chloride aerosol provides an efficient utilization of copper to form the active Cu-Si alloys on the silicon particles' surfaces. Also disclosed in a new, integrated production process which consists of methods to produce the copper chloride aerosol and feeding the aerosol into various mechanical mixing devices in which a particle size distribution of silicon can thoroughly make contact with the aerosol to form the active contact mass in one step.

16 Claims, No Drawings

METHOD FOR MAKING A SILICON/COPPER CONTACT MASS SUITABLE FOR DIRECT REACTION

BACKGROUND OF THE INVENTION

1. Field of the Invention

This invention relates to a method to prepare active silicon/copper contact mass for the direct reaction of organic halides with silicon to make organohalosilanes. More particularly, this invention utilizes vapor of a copper catalyst, namely copper chloride, or extremely fine aerosol of a copper catalyst, namely copper chloride, to prepare the active contact mass.

2. Description of the Prior Art

Organohalosilanes, especially methylchlorosilanes, are well known reactive chemical intermediates used extensively in the silicone industries. The direct reaction of silicon with organic halide to produce the corresponding organohalosilanes was first disclosed by Rochow in the United States in 1945 and, at about the same time, by Muller in Germany. The direct combination of silicon and organic halides to produce organohalosilanes is unique and, hence, it is generally referred to as the "direct reaction," the "direct synthesis" or the "direct process". Rochow's process was a significant development from the prior, much more dangerous Grignard reaction for producing silanes on a large commercial scale. The direct reaction is practiced by major silicone manufacturers which produce virtually all commercial organohalosilanes in the work today. Since the early work of Rochow, the direct reaction for producing organohalosilanes has been modified and refined in many ways to improve the overall process efficiency and better utilization of raw materials. In the modern manufacture of silicones, hundreds of million pounds of organohalosilanes, methylchlorosilanes in particular, are produced annually worldwide by the direct reaction. Thus, even a small increment of improvement in the direct reaction can have a significant economic impact on the manufacturing of silicone products and, therefore, would be quite attractive to the manufacturers.

It is important to note that many organohalosilanes are produced in the direct reaction of a organic halide with silicon. For example, the direct reaction of methyl chloride and silicon produces minor amounts of tetramethylsilane, trichlorosilane, dimethylchlorosilane, silicon tetrachloride and larger amounts of methyldichlorosilane, trimethylchlorosilane, methyltrichlorosilane, dimethyldichlorosilane and methylchlorodisilanes. In modern product processes the largest volume silane manufactured is dimethyldichlorosilane which is the most useful raw material for most of the high volume commercial silicone products after it has been hydrolyzed and condensed to the siloxane form from which the term "silicones" is derived. On the other hand, the second largest volume silane produced is methyltrichlorosilane which is the least useful. The bulk of methyltrichlorosilane produced has been simply destroyed in the past when environmental protection was lax and waste disposal was inexpensive. Today this large excess methyltrichlorosilane is often sold at below manufacturing cost to make low products such as fume silica. Those skilled in the art are interested in the selectivity of the direct reaction particularly in the formation of dimethyldichlorosilane, $Me_2SiCl_2$, in comparison with the least desirable methyltrichlorosilane, $MeSiCl_3$. The selectivity is expressed as the ratio of methyltrichlorosilane to dimethyldichlorosilane in the crude reaction product mixture. A smaller ratio indicates less amount of the methyltrichlorosilane produced. Generally this ratio is also referred to as $Me/Me_2$ (from the number of Me groups in the chemical formula) or T/D (from the name tri-chloro and di-chloro). For the purpose of this invention the selectivity is indicated as T/D. To the silicone manufacturers it is important to carry out the direct process to maximize the production of dimethyldichlorosilane or, conversely, to achieve a smaller value of the T/D ratio which indicates an increase in the output of the preferred dimethyldichlorosilane with a corresponding decrease of the least desirable methyltrichlorosilane.

Rochow in U.S. Pat. No. 2,380,995 issued Aug. 7, 1945 showed that the direct reaction of methyl chloride with silicon at about 300° C. yields a silane mixture which was predominantly methyltrichlorosilane and dimethyldichlorosilane with a T/D ratio of 3.6. Rochow also discloses the use of a 50/50 weight ratio of silicon-copper alloy and the use of metallic catalysts other than copper, such as nickel, tin, antimony, manganese, silver and titanium. Rochow and Gilliam in U.S. Pat. No. 2,383,818 issued Aug. 28, 1945 disclose the use of contact masses prepared from silicon and an oxide of copper. Ferguson and Sellers in U.S. Pat. No. 2,443,902 issued Aug. 28, 1948 disclose a method to increase the yield of dialkyldihalosilanes from the direct reaction of alkyl halide and silicon in the presence of a finely divided cuprous catalyst, having the major constituent of the metallic copper core surrounded by a protective film of cuprous oxide on its surface. Two examples cited in the patent on the direct reaction of methyl chloride and silicon in the presence of the copper catalyst show T/D ratios of 0.18 and 0.77, respectively. Gilman in U.S. Pat. No. 2,464,033 issued Mar. 8, 1949 discloses the use of copper halides, in addition to copper metal and copper oxides, as catalysts in the direction reaction. Further, this patent discloses the use of promoters, such as zinc, zinc halide or their mixture. Improved T/D ratios ranging from 0.20 to 0.40 were demonstrated in the direct reaction of methyl chloride and silicon in the presence of the copper catalyst and zinc promoter.

Soon after Rochow's discovery, it was quickly recognized that the direct reaction is a viable commercial process to produce large quantities of the dimethyldichlorosilane and other useful methylchlorosilane monomers to make a class of completely new, siloxane polymeric materials which are generally called silicones. What followed were many new products and new uses of silicones which usages have rapidly grown to become the large, profitable business known as the silicone industry today. The direct reaction is the key production process which produces, directly or indirectly, all the starting organochlorosilanes used by the silicone industries. Since the early work of Rochow, the direct reaction has been refined in many ways to improve process efficiency and raw material utilization by improving selectivity with higher dimethyldichlorosilane yield. The teaching of the prior art on the direct reaction can be found in many publications an in textbooks, for example, ΘOrganosilicon Compounds" by C. Eaborn, Butterworth Scientific Publications, London, 1960; "Synthesis of Organosilicon Monomers" by a. D. Petrov, B. F. Mironov, V. A. Ponomarenko and E. A. Chernyshev, Consultants Bureau, New York, 1964; and "Organohalosilanes: Precursors to Silicones" by R. J. H. Voorhoeve, Elsevier Publishing Company, New York, 1967. The teaching of the prior art concludes that copper is the most important catalyst for the direct reaction of methyl chloride and silicon to produce the methylchlorosilane monomers. Without copper, the performance of the direct reaction is so poor that it would have no commercial value by present day standard. Therefore, every silicone manufacturer who practices the direct reaction utilizes a copper catalyst in its production process. This mixture of silicon and copper catalyst used in the direct reaction is generally called the silicon/copper contact mass or, the contact mass in short. The performance of the silicon/copper contact mass in the direct reaction is also enhanced by the presence of other elements generally known as promoters. Examples are zinc, tin, antimony, cadmium, and phosphorous to name a few. Even after more than forty years since Rochow's discovery of the direct reaction, new promoters are still being discovered. Halm et al in U.S. Pat. No. 4,762,940 issued Aug. 9, 1988 disclose metal arsenides and alloys of arsenic as promoters for the direct reaction to prepare alkylhalosilanes. However, the utilization of copper as an absolutely indispensable catalyst for the direct reaction remains unchanged to the present time. As taught in the prior art, one of the most important steps to carry out an efficient direct reaction for the production of methylchlorosilane monomers is the preparation of a good contact mass from silicon and the copper catalyst.

SUMMARY OF THE INVENTION

The inventor herein found that his new method of preparing active silicon/copper contact mass when used as described gives an improved performance of the direct reaction for the manufacturing of organohalosilanes. This new method consists of various ways to generate a copper catalyst, preferably copper chloride in a vapor or extremely fine copper catalyst aerosol produced by rapid nucleation of the vapor. The copper catalyst aerosol is directly fed into various mechanical mixing devices where a particle size distribution of silicon can thoroughly make contact with the aerosol at the normal reaction temperature to form the active contact mass in one step. This new integrated process to produce active silicon/copper contact mass for the direct reaction has many benefits. The particle size, 0.1–0.01 micron and smaller, of the copper catalyst aerosol so produced is much smaller than that of the particle size, 1–20 microns, of the conventional copper catalysts presently used by the industry in the direct reaction to make the methylchlorosilane monomers for the production of silicones. The much smaller copper catalyst aerosol results in much less copper required being at about one-tenth or less than that of the amount of copper normally used to prepare the active silicon/copper contact mass for the direct reaction as taught by the prior art. The results are a large savings in the cost of copper catalyst in the production process and on the cost of subsequent waste disposal of the spent copper. The benefits of the active silicon/copper contact mass produced by this invention are a better performance of the direct reaction of methyl chloride and silicon to make methylchlorosilanes, namely better selectivity toward the most useful dimethyldichlorosilane, higher raw material utilization and improved process efficiency, such as, a constant reaction rate and longer life of the contact mass bed in a continuous production run due to the presence of the much-less-than-normal copper content in the reactor.

The new, integrated process of this invention to prepare the active silicon/copper contact mass utilizes a cuprous chloride vapor and/or aerosol generator in conjunction with a mechanical mixing device in which a particle size distribution of silicon can thoroughly make contact with the cuprous chloride vapor/aerosol at the normal reaction temperature to form the active contact mass in one step. One benefit to be derived from using this instant invention is a very large reduction of the amount of copper catalyst needed in the direct reaction of organic halides with silicon to make organohalosilanes.. The result is a large savings in the cost of copper catalyst and in the cost of subsequent disposal of the spent copper wastes. Other benefits are a more active contact mass to give better performance of the direct reaction in terms of better production rate, selectivity of certain organohalosilanes over other less-preferred organohalosilanes, and higher utilization of raw material. The much-less-than-normal copper concentration in the contact mass bed inside the reactor can also significantly improve the longevity of the production run resulting in higher process efficiency and better utilization of silicon.

At the beginning of the process of this invention, one starts with silicon which is grounded to a desired particle size distribution. The silicon used by most silicone manufacturers is a general grade called metallurgical silicon which contains about 98% to 99% elemental silicon. Typical particle size distribution of silicon is about 50 microns to 500 microns range. Next, one starts with a copper catalyst which can be copper metal or a copper compound, such as cuprous chloride and copper oxides. The copper catalyst so-called is not yet an active catalyst for the direct reaction since it must combine with silicon on the silicon particle surfaces to form the catalytically active copper-silicon, Cu-Si, alloys. In order to form these active Cu-Si alloys uniformly and efficiently on the silicon particles' surfaces, the copper catalyst whether it is copper metal or a copper compound is usually in the form of finely divided particles about 1 to 20 microns in size. To prepare the active silicon/copper contact mass for the direct reaction, one needs to perform an important step to bring the silicon particles and the much finer copper catalyst particles together in a certain manner under certain reaction conditions so that the copper catalyst can interact with silicon to form the catalytically active Cu-Si alloys on the silicon particles' surfaces. Those skillful in the art realize that this interaction is a very important step since the quantity as well a the quality of the Cu-Si alloys formed on the silicon particles' surfaces will ultimately determine the performance of the direct reaction for the production of the useful methylchlorosilane monomers. The entity Cu-Si represents a class of catalytically active species for the direct reaction. The term alloy is used to indicate its physical and chemical nature, such as the formation of a metallic bond between copper atoms and silicon atoms. As taught by the prior art, more than one Cu-Si alloys are known active catalysts for the direct reaction. The most studied one is the intermetallic compound, $Cu_3Si$. In the presence of Cu-Si alloys, this mixture of silicon and copper, called a contact mass, is now active toward methyl chloride to produce methylchlorosilanes at temperatures about 280° C. to 350° C. range. In the literature, there are disclosed many different methods to prepare active contact mass for the direct reaction. In some cases the active contact mass is generated in the same reactor for the direct reaction during the production process. This method is the simplest, but the conditions to form the Cu-Si alloys are limited to the same conditions as the direct reaction. In other cases, the active silicon/copper contact mass is prepared in a separate step and then fed into the reactor for the direct reaction. This separate step costs more, but it allows one to choose the optimum conditions to form the Cu-Si alloys. The result can be a better silicon/copper contact mass to substantially improve the direct reaction. This improvement for the production process can often outweigh the cost of the separate step to make the active contact mass. The application of a promoter, such as zinc, to the contact mass to enhance the direction reaction is not as critical as that of copper. Here, the zinc promoter can be added during the preparation of the active silicon/copper contact mass, or it can be separately added into the reactor for the direct reaction during the production process.

The physical and chemical properties of the copper catalyst, whether it is copper metal or a copper compound, are important factors in the preparation of active contact mass for the direct reaction. Those skillful in the art realize that the particle size of the copper catalyst is a critical factor. In general, the smaller the particle size, the better is the coverage and distribution of copper onto the surface of the silicon particles. For example, suppose one takes one copper catalyst particle which has a spherical shape with a diameter of two microns and places it on a silicon particle surface. Then, one applies the reaction conditions to form the active Cu-Si alloy. One can visualize that the surface contact between the surface of the copper catalyst particle and the surface of the silicon is where the active Cu-Si alloys are produced. Suppose one takes the same copper catalyst but with a smaller size, say, one micron instead of two micron in diameter. To keep the weight of the copper catalyst the same, one now has eight particles of one micron copper catalyst to give the same weight as one particle of the two micron copper catalyst. These eight particles of copper catalyst can make contact with the silicon surface at eight different locations. With the same weight percent copper catalyst loading, the smaller particle size copper catalyst can therefore give a wider coverage as well as more Cu-Si alloys on the silicon particles' surface than those of a larger particle size copper catalyst. To put some quantitative number on the question of surface are contact, one can make a hypothetical assumption that the copper catalyst particle is a perfect cube with 2 micron edges. One also assumes that the surface of silicon is perfectly flat. When this 2-micron copper catalyst cube is laid flat on the silicon surface, the surface-to-surface contact is exactly $2 \times 2 = 4$ square microns. Suppose one takes the same copper catalyst cube with one micron instead of two micron edges. To keep the same weight as the two micron cube, one now has eight copper catalyst cubes with one micron edges. Each of the eight cubes can make contact with the silicon surface at eight different locations. The eight one micron copper catalyst cubes give a total surface contact of 8 square microns which is two times the 4 square microns surface contact provided by a two micron copper catalyst cube. If the particle size of the copper catalyst is greatly reduced further to 0.1 micron or 0.01 micron, the coverage and the number of Cu-Si alloys on the silicon particles' surfaces can be increased many, many times in comparison with those of a 2 microns copper catalyst at the same weight percent loading. Conversely, much less weight of the 0.1 or 0.01 micron size copper catalyst is needed in order to give the same amount of coverage and the same number of Cu-Si alloys on the silicon particles' surfaces as the 2 microns size copper catalyst.

The particle size of commercially available copper catalyst is approximately in the 1 to 20 microns range. As disclosed in the prior art, finely divided copper oxides catalyst used to prepare the active contact mass for the direct reaction have a particle size about 1 to 10 microns. This particle size range is inherently the result of the manufacturing process used to make the copper oxides catalyst. Finely divided particles of copper catalyst can also be made by mechanical devices, such as a ball mill or a jet mill. Ward et al disclose in U.S. Pat. No. 4,500,724 and in article entitled "Catalyst of the Rochow Direct Process," Journal of Catalyst, 100, 240-249 (1986) the preparation of an active contact mass for the direct reaction with 5% by weight of cuprous chloride catalyst. The disclosed cuprous chloride catalyst has a particle size of 2 to 5 microns. The particle sizes of 1 to 20 microns are fairly typical of the copper catalysts which are used to make the active contact mass for the direct reaction in a production process. Although particle size substantially less than 1 micron is achievable, there is an inherent problem associated with sub-micron size copper catalyst 0.1 to 0.01 micron or smaller. As the particle size is reduced to this extremely fine state, the surface energy is greatly increased to exhibit properties of a different class of substance called colloids. A colloid is defined by the Webster's Dictionary as a gelatinous substance made up of very small, insoluble, nondiffusible particles larger than molecules but small enough so that they remain suspended in a fluid medium without settling to the bottom. An aerosol is defined as a suspension of colloidal particles in a gas. Examples of aerosols are smoke coming out of a stack, smog or haze in the sky produced by nucleation of pollutants in the atmosphere. When these extremely fine particles are collected in a container, the large surface energy naturally causes the particles to strongly stick together to form larger aggregates. In the preparation of active contact mass, these aggregates merely function as much larger copper catalyst particles. Indeed, aggregates are present in the 1 to 10 microns commercial copper oxides catalyst when it is examined under an electron microscope. In other words, although one can make sub-micron size copper catalyst, the natural behavior of very fine particles to form much larger aggregates can prevent one from taking advantage of their smaller size in the contact mass preparation. Another serious problem associated with sub-micron size particles is that they are very difficult to handle. For example, even a very slight movement of air can cause these particles to become airborne, resulting in a serious containment problem during transportation and utilization. While those skillful in the art could recognize the advantage of having smaller particle size, in the prior art there is no good practical method to prepare and to use sub-micron size copper catalyst in the preparation of active silicon/copper contact mass for the direct reaction. What is disclosed in this instant invention is a practical method to prepare a sub-micron size copper catalyst in the form of an aerosol produced by rapid nucleation of a vapor. The sub-micron size copper catalyst particles in the aerosol are, of course, not collected but immediately used to make the active contact mass while the individual particles are still airborne in the gaseous state. A novel, integrated production process is also disclosed by directly feeding the copper catalyst vapor/aerosol into various mechanical mixing devices containing a particle size distribution of silicon to make the active contact mass for the direct reaction in one step. As the examples of this instant invention show, many benefits can be achieved from this new method of preparing an active silicon/copper contact mass for the direct reaction in commercial production or organohalosilanes.

DESCRIPTION OF THE PREFERRED EMBODIMENT(S)

In accordance with the instant invention, my methods are disclosed herein for preparing an active silicon/copper contact mass to be used in the direct reaction for the manufacture of organohalosilanes, in particular, methylchlorosilanes. For the purpose of this instant invention, the term "copper catalyst" means the source of copper, i.e., copper metal or copper compounds, such as copper oxides and cuprous chloride used to make active silicon/copper contact mass for the direct reaction as taught by the prior art. These copper catalysts are distinguished from the terms "copper-silicon alloys," "Cu-Si alloys" or "Cu-Si catalyst," which are generally used by those skilled in the art to describe the true catalytic species for the direct reaction. In other words, the copper catalyst is not yet a catalyst for the direct reaction until it makes contact on the silicon surfaces and is activated under certain conditions to form the Cu-Si alloys. The terms "active silicon/copper contact mass" or "contact mass" in short used in this instant invention mean the resulting particles size distribution of silicon which has been physically and chemically interacted with the copper catalyst to form sufficient Cu-Si catalyst sites on the silicon surfaces. The contact mass so produced is naturally active toward methyl chloride in the direct reaction at temperature range of 280° to 350° to produce methylchlorosilanes. As taught by the prior art, the direct reaction is enhanced by the presence of other elements generally called promoters. Examples are zinc, tin, antimony, cadmium, arsenic and phosphorous to name a few. These promoters can be added during the preparation of the active silicon/copper contact mass or they can be separately added during the course of the direct reaction. Although promoters can enhance the direct reaction in various ways, they cannot function alone without copper.

The invention disclosed herein can be described in three related areas, namely (1) the methods to generate the copper catalyst vapor and aerosol, (2) the mechanical mixing devices to provide thorough contact of a particle size distribution of silicon with the copper catalyst vapor/aerosol and (3) an integrated production process with the above methods and devices to prepare a large amount of the active silicon/copper contact mass for the direct reaction in the manufacturing of organohalosilanes, and in particular, methylchlorosilanes.

(1) Methods to Make Copper Catalyst Vapor and/or Aerosol

Copper metal itself with very high boiling point (b.p.) at 2567° C. is considered as being non-volatile. There are copper compounds which boil at temperatures which can be readily achieved by conventional means. Thus, vapor and aerosol of copper catalyst can be readily produced by heating a volative copper compound at these temperatures. The most volatile copper compounds are the copper halides. Copper halides exist in two valent states, namely, the mono-valent cuprous halide [or copper (I) halide] and the di-valent cupric halide [or copper (II) halide]. In the Handbook of Chemistry and Physics, CRC Press, 1979, the boiling points of the cuprous halides are listed as copper (I) fluoride, b.p. 1100° C. (sublimed); copper (I) chloride, b.p. 1490° C.; copper (I) bromide, b.p. 1345° C.; and copper (I) iodide, b.p. 1290° C. These temperatures can be readily attained by conventional heating devices, such as electrical resistance heaters and induction heaters. Also, one may not need to heat the cuprous halide to its boiling point, since a substantial vapor pressure can be generated at considerably lower temperatures. For example, cuprous chloride exhibits a vapor pressure of 100 mm (mercury) at 960° C. Thus, a 13% by volume of cuprous chloride vapor can be produced by passing an inert gas at 960° C. over a cuprous chloride liquid at atmospheric pressure, 760 mm (mercury). Cupric halides decompose at a temperature approximately above 900° C. to the cuprous halides. There is another advantage of using cuprous halides to prepare the active silicon/copper contact mass for the direct reaction. Cuprous halides are naturally reactive toward silicon to form the Cu-Si alloys. For example, cuprous chloride is well known in the prior art to readily react with silicon at temperatures above 260° C. to form the Cu-Si alloys and silicon tetrachloride. Cuprous chloride is among the most useful copper catalyst used to make the contact mass for the direct reaction in the production of methylchlorosilanes. Cuprous chloride is commercially most readily available at the lowest cost of the cuprous halides. Furthermore, chloride is much more environmentally acceptable than those of the fluoride, bromide and iodide in terms of waste disposal. Therefore, cuprous chloride is preferred copper catalyst for the preparation of active silicon/copper contact mass.

Various methods to generate a copper catalyst vapor and/or aerosol for the preparation of active silicon/copper contact mass can be utilized. For example, cuprous chloride vapor and/or aerosol can be produced simply by heating cuprous chloride in a container at a sufficiently high temperature to evaporate or to boil off the material. An inert gas, such a nitrogen or argon, may be used to carry the cuprous chloride vapor/aerosol out of the container downstream for the preparation of the active contact mass. A copper chloride aerosol may also be prepared by a strongly exothermic chemical reaction. For example, copper metal is known to burn in chlorine gas. When a finely divided copper metal is injected into hot chlorine gas, the copper metal can be seen to burst into a bright orange flame to produce a cloud of white smoke being an aerosol consisting of mostly extremely fine cuprous chloride particles. The strongly exothermic reaction produces very high temperature which vaporized the cuprous chloride product. Subsequent cooling causes rapid nucleation of the vapor to form the extremely fine cuprous chloride as seen by the white smoke. Aerosols of other copper catalysts can also be generated by other physical means, such as that of a high pressure spray nozzle and ultrasonic vaporizer. The widely used consumer product, the cool mist humidifier, is operated by the principle of ultra sound. The intensive ultrasonic energy breaks up the liquid water to produce a fine mist also being an aerosol which rapidly evaporates in the atmosphere to provide the humidity. A solution of a copper compound dissolved in water or in any other solvents can be converted to an aerosol by this type of ultrasonic device. There are a large number of copper compounds, such as copper chloride, copper nitrate, copper sulfate, etc., which are soluble in water. A aqueous solution of these copper catalysts can be used in these ultrasonic devices to produce an aerosol which may be dehydrated while it is still airborne. The partially and/or completely dehydrated copper catalyst aerosol can then be used to prepare the active silicon/copper contact mass for the direct reaction. Experiments in the laboratory have been carried out to test and to prove validity and commercial usefulness of the novel ideas disclosed in this instant invention. The following examples only provide the technical results for discussion and should not be considered to necessarily limit the scope of this invention.

EXAMPLE 1

Cuprous chloride is a readily available commercial product. A small quantity of pure cuprous chloride can be readily prepared by a number of laboratory procedures as described in "A Text-book of Inorganic Chemistry," J. R. Partington, sixth edition, MacMillan and Co., Ltd., London, 1957. Sulfur dioxide gas is passed into a solution of 250 grams of crystallized copper sulfate and 120 grams of sodium chloride in 700 milliliters of distilled water. Cuprous chloride slowly crystallizes out as a white precipitate. It is filtered through a dropping funnel equipped with a glass fritted disc at the bottom. The white cuprous chloride powder collected is washed with several portions of distilled water saturated with sulfur dioxide. It is dried inside the dropping funnel by a vacuum pump equipped with a water-absorbing trap. The dried cuprous chloride (about 60 grams) is stored in the dropping funnel under nitrogen. A sample of this cuprous chloride is charged into a large test tube with a sealed 8 millimeter (mm) inside diameter glass tube attached to the bottom. This glass apparatus is placed inside an enclosed electric heater under nitrogen gas. The cuprous chloride, melting point 422° C., is melted under nitrogen at about 460° C. The molten cuprous chloride flows down into the small glass tube at the bottom and is cast into a solid rod about 8 mm in diameter after cooling to room temperature. The almost colorless, wax-like cuprous chloride rod is taken out of the glass tube by breaking it. The solid cuprous chloride rod is broken into small pellets and stored in an atmosphere of dry nitrogen inside a glove box.

An apparatus to test the method to make cuprous chloride vapor and aerosol is constructed. It consists of a one inch diameter by 12 inches long laboratory tube furnace and a small quartz tube 18 mm (0.71 inch) in diameter by 18 inches in length. A small indentation one inch from the front end of the quartz tube is made by heating the wall with a torch while another one is made at the same side of the wall seven inches from the front. The indentations are designed to keep the cuprous chloride liquid from flowing out from either side of the quartz tube. Pieces of the solid cuprous chloride pellet, 8.1 grams, are placed inside the quartz tube in between the two indentations at the bottom side of the quartz tube. The quartz tube containing the cuprous chloride is weighed and recorded. A gentle flow of argon gas is fed at the rear end of the quartz tube through an inlet assembly. After air inside the quartz tube has been replaced by argon, the quartz tube is inserted into the laboratory tube furnace already heated to about 1200° C. Soon, white smoke made up of cuprous chloride aerosols flows out of the quartz tube and is quickly dispersed into the atmosphere. After three minutes, the amount of smoke appears to subside. The heater is turned off and the quartz tube is removed and weighed. The difference in weights before and after heating shows 6.8 grams of the cuprous chloride have been evaporated to produce the aerosol in about three minutes. This gives a production rate of cuprous chloride aerosol at about 2.7 grams per minute or 0.3 pound per hour.

EXAMPLE 2

A small funnel consisting of a one inch diameter by two inches in length copper tube is constructed. The bottom of the funnel is fitted to a chrome plated brass tube which is plugged at the bottom end. A sample of the cuprous chloride powder prepared in EXAMPLE 1 is charged into the funnel and placed inside the electric heater. The contents are heated to about 460° C. under an atmosphere of nitrogen. The molten cuprous chloride is collected and fills the 8 mm diameter chrome plated brass tube at the bottom. After cooling to room temperature the portion of the 8 mm tube is cut out at the point where solid cuprous chloride completely fills the tube. The result is an electrode 8 mm in diameter by six inches long with a center core of solid cuprous chloride. This electrode is mounted upright in a turning table at which the negative pole of an automobile battery is attached to serve as the cathode. A graphite rod mounted on an insulator on top of the cuprous chloride cathode is attached to the positive pole of the battery to serve as the anode. The turntable spins the cuprous chloride cathode at about 60 revolutions per minute (rpm). The turntable is also lifted up toward the stationary graphite anode at about 0.5 inch per minute by a small geared motor assembly. An electric arc is produced when the cuprous chloride filled cathode touches the graphite anode. The high temperature produced by the electric arc rapidly vaporizes the cuprous chloride as seen by puffs of white smoke of cuprous chloride in an aerosol state. A continuous production of the cuprous chloride aerosol is obtained as the cathode is slowly raised and consumed by the electric arc. This test shows that a copper catalyst vapor and/or aerosol can also be prepared by other heating devices, such as the electric arc or plasma arc set forth in this example. In practice, one may need to confine the electric arc in some kind of conduit where a constant flow of inert gas can be used to carry the copper catalyst aerosol downstream for the preparation of active silicon/copper contact mass for the direct reaction.

EXAMPLE 3

An apparatus is constructed to test the production of cuprous chloride aerosol by the rapid, exothermic reaction of copper metal with chlorine gas. A burner resembling an oxyacetylene cutting torch is constructed with a small tubing mounted at the center and inside an outer jacket. At the outlet end of this jacket are eight small holes which are arranged in a concentric manner around the opening of the center tubing. In the oxyacetylene torch, oxygen exits at the center hole while an envelope of acetylene gas coming out of the surrounding holes provides good mixing of the burning gas. In this laboratory apparatus, the fine copper metal powder is pushed out by a burst of nitrogen at the center hole through the center tubing while hot chloride gas coming out of the eight concentric holes of the outer jacket forms a tight envelope which completely surrounds the puff of fine copper metal powder. The jacket assembly is electrically heated to temperature approximately 280° C. to 350°0 C. The center tubing is connected to a small ball valve at the bottom end. The top end of the ball valve is connected to a Pyrex glass, three-way capillary stopcock at the common end. The small space between the ball valve and the capillary stopcock can trap a volume of about 0.3 to 0.5 gram of a −325 mesh copper metal powder. One of the two capillary inlet tubes on the top of the three-way stopcock is connected to a small funnel where the fine copper metal powder is stored. The other inlet tube of the stopcock is connected either to a vacuum pump or to a source of nitrogen gas at about 8 psig (pound per square inch gauge) pressure. To operate the copper powder feed, the ball valve is closed while the three-way stopcock is turned to the side connecting the vacuum pump. The small space between the ball valve and the stopcock is evacuated with a vacuum pump. The three-way stopcock is then turned 180 degrees to connect the other inlet where the fine copper metal powder is stored. The action of the vacuum sucks in the copper powder to fill the small space between the stopcock and the ball valve. The three-way stopcock is again turned 180 degrees back to the inlet where the vacuum pump is now replaced by a charge of nitrogen gas at about 8 psig. By quickly opening the ball valve, the nitrogen pressure pushes the small volume of copper metal powder through the center tube of the burner and squirts out in a small puff. Chlorine gas from a cylinder is fed through a flow meter into a heated stainless steel cylinder at about 280° C. to 350° C. The hot chlorine gas is fed from the side into the jacket of the burner where it exits through the eight small holes surrounding the outlet of the center tube for the copper metal powder feed. A Pyrex tube, 1.5 inches in diameter by 12 inches in length is fitted to the front of the burner. This Pyrex tube serves as a combustion chamber. It is also heated by a glass electrical heating jacket at about 280° C. to 350° C. To operate the burner, a small volume of about 0.4 gram of the −325 mesh copper metal powder is pressurized with 8 psig of nitrogen and ready to use. Chlorine gas is fed at a rate of about 8 liters per minute through the eight small holes for a brief moment to fill the heated Pyrex tube combustion chamber with hot chlorine gas. The ball valve is then quickly opened to squirt a puff of the copper powder into the combustion chamber filled with fast-flowing, hot chlorine gas at about 320° C. A bright flash of orange flame is seen through the glass wall while a cloud of white smoke is seen shooting out at the other end of the Pyrex tube. The white smoke of copper chloride aerosol rises up and disperses into the surrounding atmosphere. A filtering device attached to a vacuum pump is used to collect a sample of the copper chloride aerosol in the white smoke. Examination of the sample under an electron microscope shows a variety of solid particles and aggregates. The size of the individual particles appears to be mostly in the range of about 0.1 to 0.01 micron and smaller. The copper chloride aerosol produced by this unique combustion process can be directly used for the downstream preparation of the active silicon/copper contact mass for the direct reaction.

(2) The Mixing Mechanical Devices

The copper catalyst aerosols prepared by the methods of EXAMPLE 1, EXAMPLE 2 and EXAMPLE 3 are not collected and stored for later use. The novel idea in this instant invention is to put these extremely fine, sub-micron size copper catalyst particles onto the silicon surfaces while the particles are still individually suspending in the gaseous state in the aerosol. To accomplish this, a mechanical mixing device is used to provide thorough contact of the copper catalyst aerosol with the individual silicon particles. In the case of the cuprous chloride aerosol, the particle size distribution of silicon in the mechanical device can also be heated to the reaction temperature range at about 260° C. to 350° C. At this temperature range cuprous chloride rigidly reacts with silicon to form the active copper-silicon alloys on the silicon particles' surfaces. In order to avoid the sub-micron size cuprous chloride particles sticking together to form larger aggregates, the cuprous chloride aerosol is immediately used as soon as it is generated in the downstream preparation of the silicon-copper contact mass for the direct reaction. A variety of mechanical mixing devices can be used to accomplish the task of preparing the active contact mass.

An example of a good mechanical mixing device is that of a scrubber. Harmful fine dust pollutant in the air can be effectively cleaned up by scrubbing them in a spray tower. Here, fine droplets of water, or reactive chemical in a solution, provide large surface areas to interact with the fine dust and pollutant. The fine dust or pollutant in contact with the water droplets surface are removed from the polluted air. The particle size distribution of silicon used in the direct reaction for the production of methylchlorosilanes also consists of rather small silicon particles comparable to the fine water droplets produced by the spray tower scrubber. Ward et al in U.S. Pat. No. 4,500,724 issued Feb. 19, 1985 disclose that the silicons used in a fluidized bed reactor can have a particle size below 700 microns; with an average particle size greater than 20 microns and less than 300 microns; preferably with mean diameter of 100 to 150 microns. One micron is equal to 0.000039 inch. In this spray tower embodiment, the silicon used to prepare the contact mass can be spread and dropped from the top of a tall reactor or tower while the copper catalyst aerosol is fed from the bottom of the reactor. The extremely fine, 0.1 to 0.0 micron and smaller, cuprous chloride particles in the aerosol are scrubbed and removed from the carrier gas. The reactor and the silicon may also be heated to the temperature range of about 260° C. to 350° C. to cause rapid reaction between cuprous chloride and silicon to form the Cu-Si alloys on the silicon particles' surfaces. In this manner, the cuprous chloride aerosol is not only physically, but also chemically scrubbed. The formulation of Cu-Si alloy bonds the aerosol particles onto the silicon surface to achieve what is need in an active contact mass for the direct reaction. The silicon tetrachloride by-product from the cuprous chloride reaction with silicon remains in the gaseous state and is removed from the reactor with the carrier gas. The amount of silicon falling from the tall reactor and the rate of feeding the cuprous chloride aerosol are kept at a constant rate to provide a continuous production of the active contact mass. It is well known to those skillful in the art that the copper catalyst must be deposited onto the silicon particles' surfaces in a uniform manner. It is desirable that every individual silicon particle in the contact mass have the same Cu-Si alloy concentration deposited on its surface. In other words, the mechanical mixing device provides the same amount of the cuprous chloride aerosol on every individual silicon particle in the contact mass.

Another mechanical mixing device which can provide very uniform treatment of the silicon particles with the cuprous chloride aerosol is similar to that of a rotatory calciner design. Rotary calciners are commonly used in industrial processing equipment. Basically, it consists of a rotating cylinder with internal fins. The solid materials to be treated in the calciner are lifted up by the rotating fins. As the solid materials continuously fall down from the upward movement of the fins, a shower of the solid materials completely fills the inside space of the rotating cylinder. Such mechanical motion is quite suitable for the treatment of silicon particles with the cuprous chloride aerosol in the a slow flowing carrier gas. The rotatory calciner mixing device is particularly suitable for large scale, continuous production of active silicon/copper contact mass. In a continuous operation, the rotating cylinder can be lifted at a slight inclination at the inlet end. The particle size distribution of silicon can be fed at the inlet end while the rotating action of the cylinder slowly moves the silicon toward the outlet end and is withdrawn from the cylinder. In this manner, every individual silicon particle has gone through the same path inside the rotating cylinder and, thus, has been exposed to more or less the same amount of cuprous chloride aerosol. The cylinder containing the silicon can also be heated to the temperature range of about 260° C. to 350° C. to cause rapid reaction between the cuprous chloride and the silicon to form a uniform deposition of the Cu-Si alloys onto the silicon particles' surfaces. A mechanical mixing device similar to that of a rotatory calciner design provides a practical industrial processor to prepare active silicon/copper contact mass with the novel copper catalyst aerosol concept set forth in this instant invention.

The fluidized bed reactor used to carry out the direct reaction for the production of methylchlorosilanes is itself a good mechanical mixing device. The stirred bed reactor designed to operate close to the minimum fluidization velocity is also suitable for the treatment of the silicon particles with cuprous chloride aerosol to prepare the active contact mass at the temperature range of about 280° C. to 340° C. normally used for the direct reaction. A laboratory apparatus to test such mechanical mixing device for the preparation of an active silicon/copper contact mass was constructed and studied as described in EXAMPLE 4 below. The various mechanical mixing devices described above are to demonstrate the validity of the new method to make a contact mass and should not be felt to limit the scope of this invention.

EXAMPLE 4

A laboratory apparatus is constructed to test the rotatory calciner mixing device for the preparation of active silicon/copper contact mass for the direct reaction to produce methylchlorosilanes. A rotatory cylinder is built from a 6-inch diameter stainless steel tube. Two 6-inch diameter flanges are fitted to both ends to form a cylinder. Inside the cylinder are installed four equally spaced fins ¾ inch high parallel to the entire length of the cylinder. The flange at the front end is attached to a large bore, ball bearing mounted on a sturdy post. An opening at the center of the flange provides the inlet and connection to the source of cuprous chloride aerosol generated by the methods described in EXAMPLE 1 and EXAMPLE 3. The flange at the rear of the cylinder is fitted with a piece of 1-inch diameter by 6-inch long copper tube at the center and parallel to the length of the cylinder. The copper tube is fitted to a ball bearing which is mounted on a sturdy post. The posts are fixed onto a ¼ inch thick aluminum base plate such that the cylinder lies horizontally on the two supporting ball bearings. A belt and pulley are fitted to the 1-inch tube next to the supporting ball bearing. The belt is attached to a variable speed geared motor which spins the cylinder at a desired speed. The rotatory cylinder is placed inside an electric tube heater, 8 inches in diameter by 18 inches in length. The heat heats the 6-inch diameter by 18-inch long cylinder to a selected temperature at about 260° C. to 350° C. range which is the temperature for the reaction of cuprous chloride and silicon to form the Cu-Si alloys. The rotatory cylinder is set up in such a way that it can be easily installed or dismounted from the supporting posts. It can be removed from the heater for charging a particle size distribution of silicon or , for withdrawing the finished contact mass. To test the mechanical mixing device, the rotatory cylinder is charged 5 pounds of the metallurgical silicon with a particle size distribution of $50\times150$ mesh ($300\times105$ microns). The cylinder is remounted on the supporting posts. The geared motor is turned on to rotate the cylinder by the belt and pulley attachment. The behavior of the $50\times150$ mesh silicon inside the rotatory cylinder can be seen from the larger opening at the front end of the cylinder. At too fast a rotating speed, the centrifugal force keeps the silicon particles from falling down. At too slow a rotating speed, the silicon slides down from the up-lifting fins before it reaches the top of the cylinder. By adjusting the variable speed geared motor to give a rotation speed between 60 to 80 rpm, the contents are seen to tumble gently inside the cylinder with falling silicon particles completely filling the inner space. This mechanical motion provides for efficient contact between the silicon particles and the cuprous chloride aerosols. The electric tube heater is also tested by varying the power input to the heating elements to achieve the desirable temperature range at 260° C. to 350° C. as measured by a thermocouple extending to the midpoint inside the rotating cylinder. Results of this test show that the commercial rotatory calciner design can provide a thorough mixing action with good contact of the silicon particles with the surrounding gaseous phase in which the sub-micron size cuprous chloride aerosols are suspended.

(3) Preparation of Active Silicon/Copper Contact Mass for the Direct Reaction The laboratory apparatus constructed in EXAMPLE 4 is used to test the new method of an integrated process to prepare active silicon/copper contact mass for the direct reaction as set forth in this instant invention. The contact mass prepared by this new method is then tested in the direct reaction to make organohalosilanes. The organohalosilanes are those having the general formula $$(I)RSiX_{4-a},\ (II)R_bH_cSiX_{4-b-c}\ \text{and}\ (III)R_dX_{3-d}SiSiR_eX_{5-e},$$

with silanes (I) being the preferred silanes of the invention. In the above formulae, each R is independently selected from alkyl groups having 1-6 carbons of from aryl groups "a" has a value of 1, 2 or 3. X is a halogen atom, preferably a chlorine atom. In formula (II), "b" has a value of 1 or 2, "c" has a value of 1 or 2 and the sum of "b+c" cannot be greater than 3. In formula (III), "d" and "e" have a value of 1 or 2. Preferred silanes are those having the formula $R_2SiX_2$ and $R_3SiX$, wherein R is a methyl or phenyl and X is chlorine. Most preferred is the silane $Me_2SiCl_2$.

In the direct reaction of the active silicon/copper contact mass with organic halides, methyl chloride is the preferred organic halide for this invention. The silicon useful in this instant invention is any silicon having a purity of at least 50% by weight (wt %) but less than 100 wt % silicon. An example of such silicon is metallurgical silicon metal. The silicon for the purpose of this invention is particulate silicon having a particle size of 0.1 to 800 microns. The silicon has a particle size distribution known to the art to be suitable for a fluidized bed reactor. For example, Dotson in U.S. Pat. No. 3,133,109 disclosed that for optimum results in the direct reaction of methyl chloride with silicon, the particles in a fluidized bed reactor shall have an average particle size of about 20 to 200 microns. Ward et al in U.S. Pat. No. 4,500,724 disclose that silicon present in a fluidized bed can have a particulate size below 700 microns; with an average particle size greater than 20 microns and less than 300 microns; preferably with a mean diameter of 100 to 150 microns. In the new method of preparing active silicon/copper contact mass with the copper catalyst aerosol described in this instant invention, the particle size of silicon used is in the range of 105 to 300 microns (150×50 mesh) which is comparable to those disclosed in the prior art and to those used by the silicone industries today.

Direct reaction of methyl chloride with the active silicon/copper contact mass in this instant invention can be carried out in a fluidized bed reactor at a temperature range from about 250° C. to 350° C.; preferably in the range of 280° C. to 330° C. The reactor used for the direct reaction is similar to that described in Dotson, U.S. Pat. No. 3,133,109 and is familiar to those skillful in the art of producing methylchlorosilanes from the reaction of methyl chloride and silicon. In general, the reaction is carried out by passing methyl chloride gas into a mass bed of the contact mass in a fluidized bed reactor heated at an elevated temperature, for example, 320° C. The rate of methyl chloride feed needs to be sufficiently high so as to fluidized the contact mass bed to facilitate heat transfer. Provisions are provided in the reactor system so that additional fresh contact mass and promoters used to enhance the direct reaction as taught by the prior art may be added without interfering with the direct reaction in progress. The methylchlorosilane products form the direct reaction and the unreacted methyl chloride are condensed by a low temperature condenser. The methylchlorosilane products are analyzed by a gas chromatography to determine the percent compositions of each of the silane components. Samples of the reaction products are collected in regular intervals, weighed and analyzed. In this manner, the progress of the direct reaction as a function of time can be measured. From the gas chromatographic analysis of the methylchlorosilanes, the percent of each of the silane components, dimethylchlorosilane, methyldichlorosilane, trimethylchlorosilane, methyltrichlorosilane, dimethyldichlorosilane and the methylchlorodisilane heavies are determined. Those skillful in the art are interested in the selectivity of the direct reaction, which is generally expressed as the ratio of the methyltrichlorosilane to dimethyldichlorosilane or, T/D in this instant invention. The smaller the ratio the higher is the dimethyldichlorosilane yield, which is the most desirable product. The reaction rate is also an important parameter to measure the performance of the direct reaction. For the purpose of this invention, the reaction rate is expressed as the percent silicon conversion per hour or, % Si conv./hr. For example, a 1% Si conv./hr means that one percent of the silicon/copper contact mass bed has been converted to the methylchlorosilane products during one hour of the direct reaction. The amount of silicon reacted in the direct reaction at a given period of time can be calculated from the weight of the methylchlorosilane products collected during that given period of time. The conversion factor is about 4.6 grams of the methylchlorosilane products for one gram of silicon consumed. This is a good approximation to measure the reaction rate as a function of time, since it is not practical to weigh the contact mass bed while the direct reaction is in progress. For example, if one collects 13.8 grams of the methylchlorosilane products during one hour of the direct reaction with a 200 grams contact mass bed, the reaction rate during this one hour is 13.8/4.6×100/200=1.5% Si conv./hr.

EXAMPLE 5

The apparatus in EXAMPLE 1 used to generate the cuprous chloride aerosol is combined with the mechanical mixing device described in EXAMPLE 4 to form an integrated production process to prepare active silicon/copper contact mass for the direct reaction. An adapter is constructed to fit the outlet end of the 18 mm quartz tube to the inlet opening of the 6 inches diameter by 18 inches in length rotatory cylinder. A small tube attached to the side of this adapter provides an inlet for nitrogen gas used to flush out air inside the system. The cylinder is charged with 5 pounds of a metallurgical grade silicon with a particle size distribution of 65×150 mesh or, 210×105 microns. Into the quartz tube are charged 7 grams of the cuprous chloride pellets prepared in EXAMPLE 1. The pellets are placed in between the two indentations at the bottom of the quartz tube. The rear end of the quartz tube is attached to an inlet assembly which provides a gentle flow of argon gas to keep air out of the quartz tube. The one inch diameter, laboratory tube furnace is turned on. While the tube furnace is heated to the selected temperature of about 1200° C., another empty quartz tube is placed inside the tube furnace and engages the adapter to form an air-tight seal. The electric tube heater for the rotatory cylinder is turned on to heat the 5 pounds of silicon inside the cylinder to a selected temperature at 320° C. Nitrogen gas is fed at the side of the adapter to flush out air inside the cylinder. Once the selected temperatures are reached, the geared motor is turned on to spin the rotatory cylinder at a speed of 60 to 80 rpm. The empty quartz tube inside the tube furnace heated at about 1200° C. is quickly taken out and replaced with the quartz tube containing the 7 grams of cuprous chloride pellets. As described in EXAMPLE 1, the cuprous chloride vapor/aerosol so produced is carried by the argon gas into the rotatory cylinder containing the 5 pounds of thoroughly mixed silicon. Soon, white smoke is seen coming out at the exit end of the 1 inch copper tube attached to the rear end of the rotatory cylinder. The smoke is safely disposed of by feeding it into a scrubber containing a dilute solution of sodium hydroxide. Silicon tetrachloride vapor which is the by-product from the cuprous chloride reaction with the silicon is known to react with moisture in the atmosphere to form a white smoke. The presence of silicon tetrachloride is readily detected by a wetted blue litmus paper which turns red in contact with the white smoke. The white smoke may also contain cuprous chloride aerosol which may escape the scrubbing action of the thoroughly mixing silicon particles in the rotatory cylinder. After a total of about 16 minutes of operation, all the electric heaters are turned off. The geared motor is turned off to stop the rotation of the cylinder. A nitrogen inlet is attached to the exit end of the cylinder. With a gentle flow of nitrogen, the quartz tube is detached from the adapter. The rotatory cylinder is taken out of the tube heater. The finished active silicon/copper contact mass inside the cylinder is quickly cooled to room temperature under nitrogen. The contact mass is stored in a large bottle in an atmosphere of nitrogen for further experimentation. An analysis of the sample of this active silicon/copper contact mass shows that the contact mass contains 0.12% by weight of copper.

EXAMPLE 6

The contact mass containing 0.12 wt % copper prepared in EXAMPLE 5 is tested in the direct reaction with methyl chloride to make methylchlorosilanes. As taught by the prior art, promoters, such as zinc and tin, can enhance the direct reaction. Thus, 200 grams of this contact mass, 0.4 gram zinc carbonate and 0.02 gram tin oxide are charged into a small laboratory glass fluidized bed reactor. The reactor is heated to 320° C. and maintained at this temperature by a controller with thermocouple placed inside the reactor at about the mid-point of the fluidized contact mass bed. The methylchlorosilane products and the unreacted methyl chloride are condensed by a −40° C. condenser and collected in regular one hour to two hour intervals. The progress of the direct reaction is monitored by the amount of methylchlorosilanes collected and by the yields of the individual silanes obtained by the analysis with a gas chromatography. The contact mass is active right at the start of the direct reaction to produce methylchlorosilanes. There is no induction period which normally occurs when a mixture of silicon, copper catalyst and promoter is charged into the reactor to react with methyl chloride under the prescribed conditions. Those skilled in the art realize that the induction period is the reaction time needed to form the active Cu-Si alloys on the silicon particles' surfaces. Little or no methylchlorosilanes are produced from the direct reaction until the active Cu-Si catalysts are produced in sufficient numbers. The absence of an induction period in the direct reaction with the active silicon/copper contact mass prepared in EXAMPLE 5 is a good indication to show that the Si-Cu alloys are already present. The direct reaction is kept running until a steady state is reached whereby the reaction rate, the dimethyldichlorosilane yield and the selectivity level off to a more or less constant value. After the steady state is reached, the direct reaction is continued for several hours to collect data which is representative of the average reaction rate, yields of the methylchlorosilane products and the selectivity of the direct reaction. The results can be found in TABLE 1.

TABLE 1

| Copper Content | % MeSiCl$_3$ | % Me$_2$SiCl$_2$ | % Residue | T/D Ratio | % Si Conv. per hour |
|---|---|---|---|---|---|
| 0.12% | 4.70 | 89.83 | 3.08 | 0.053 | 1.1 |

The residue in TABLE 1 is the total amount of methylchlorodisilanes plus other high boiling materials with boiling points above that of dimethyldichlorosilane, Me$_2$SiCl$_2$. The results in TABLE 1 show that the performance of the direct reaction with the contact mass prepared by the new method with cuprous chloride aerosol disclosed in this instant invention is comparable to those of the contact mass previously reported in the literature with a much higher copper catalyst content. For example, Elattar, Azza A. discloses in EXAMPLE 1 European Patent No. EP 440414 A1 issued Aug. 7, 1991 a new method for preparing a contact mass which consists of 200 parts by weight of silicon, 9 parts of a copper catalyst (mixed copper oxides) and 1.2 parts of zinc carbonate. From the composition of the catalyst provided, it is possible to calculate the copper content in the contact mass disclosed by Elattar to be 3.7% by weight which is about 30 times than the 0.12% by weight of copper in the contact mass disclosed by this instant invention. In TABLE 2, EXAMPLE 2 of EP 440414 A1, Elattar disclosed the performance of the direct reaction to give 90.2% Me$_2$SiCl$_2$SiCl$_2$ and 89.7% Me$_2$SiCl$_2$, respectively for a fresh and a 4-month old contact mass. In the same table, Elattar disclosed a total % Si conv. in a 24 hour period to be 28.6% and 29.2%, respectively for the fresh and the 4-month old contact mass. This works out to give an average reaction rate of 1.19% Si conv./hr and 1.22% Si conv./hr over the 24 hour period. In EXAMPLE 3, EP 440414 A1, Elattar disclosed a variation of the method to prepare the contact mass which gives 86.8% Me$_2$SiCl$_2$ and an average reaction rate of 1.08% Si conv./hr. over a 24 hours period. These Me$_2$SiCl$_2$ yields and reaction rates disclosed by Elattar are comparable to those in TABLE 1 of this instant invention. The important point here is that the contact mass prepared by the novel, cuprous chloride aerosol method disclosed in this instant invention contains only 0.12% copper which is about 30 times less than that of the 3.7% copper in the contact mass disclosed by Elattar.

Elattar, in EP 440414 A1 did not disclose the particle size of the mixed copper oxides catalyst. However, those skillful in the art realize that the particle size of this type of mixed copper oxides catalyst is generally in the approximate range of 1 to 10 microns. On the other hand, the extremely fine cuprous chloride aerosol generated by the new methods disclosed in EXAMPLE 1, EXAMPLE 2 and EXAMPLE 3 of this instant invention has a particle size in the approximate range of 0.1 to 0.01 micron and smaller. The much smaller cuprous chloride aerosol is the reason for the much more efficient utilization of the copper catalyst in producing the Cu-Si alloys and for the much better coverage of these Cu-Si alloys on the silicon particles' surfaces. As proved by this experiment, the 0.12% copper content in the contact mass disclosed in this instant invention represents a very large reduction of the copper requirement for the direct reaction taught by the prior art.

EXAMPLE 8

Using the same apparatus set up in EXAMPLE 5, another active silicon/copper contact mass for the direct reaction is prepared under the same conditions except that the metallurgical grade silicon is replaced by a high purity, electronic grade silicon. In the electronic grade silicon, all the metallic impurities commonly existing in the metallurgical grade silicon have been eliminated. Five pounds of the 50×150 mesh (300×150 microns) electronic grade silicon metal are prepared with an air-driven hammer by crushing and sieving the coarse grains of polycrystalline silicon metal. The 5 pounds of electronic grade silicon are charged into the rotatory cylinder and treated with the cuprous chloride aerosol in the same manner as the experiment described in EXAMPLE 5. Analysis of the resulting contact mass shows 0.9% by weight of copper. Two hundred grams of this contact mass are mixed with 0.2 grams of zinc carbonate promoter by vigorously shaking the mixture in a bottle. The mixture is then charged into the same laboratory glass fluidized bed reactor and tested in the direct reaction with methyl chloride in the same manner as described in EXAMPLE 6. The contact mass bed is reactive right at the beginning of the direct reaction with no induction period observed. After a steady state of the direct reaction is reached to give a fairly constant yield of dimethyldichlorosilane and selectivity, the direct reaction is carried out for an additional 7 hours. Results set forth in TABLE 2 are those of the average of the 7 hours of reaction.

TABLE 2

| Copper Content | % MeSiCl$_3$ | % Me$_2$SiCl$_2$ | % Residue | T/D Ratio | % Si Conv. per hour |
|---|---|---|---|---|---|
| 0.09% | 3.98 | 89.54 | 3.55 | 0.044 | 0.62 |

Results in TABLE 2 show that by eliminating all the metallic impurities in electronic grade silicon, the direct reaction appears to produce a somewhat better selectivity but at a slower reaction rate in comparison with the results in TABLE 1, EXAMPLE 6 obtained from metallurgical grade silicon.

EXAMPLE 8

The apparatus constructed in EXAMPLE 3 to generate copper chloride aerosol by burning a −325 mesh copper metal powder in hot chlorine gas is combined with the mechanical mixing device constructed in EXAMPLE 4 to form an integrated process for the production of active silicon/copper contact mass for the direct reaction. An adapter with a larger opening is constructed to fit the 1.5 inch diameter Pyrex tube combustion chamber to the front inlet of the 6 inch diameter rotatory cylinder. A small tube attached to the side of this adapter provides the nitrogen gas inlet, which is used to flush out air inside the apparatus. The copper chloride aerosol is produced by firing a charge of the −325 mesh copper powder from the burner assembly into a flowing, hot chlorine gas inside the pyrex glass combustion chamber. The amount of copper powder fired in each shot is approximately 0.4 gram. The combustion of the fine copper powder in hot chlorine gas produces a puff of copper chloride aerosol which is mostly cuprous chloride because of the high temperature produced. The mechanism works like a smoking gun. Five pound of 50×150 mesh (300×105 microns) metallurgical grade silicon are charged into the rotatory cylinder. Air inside the apparatus is flushed out with nitrogen. The electric heaters are turned on. The container for the hot chlorine gas, the burner assembly and the Pyrex glass combustion chamber are heated and maintained at about 300° C. The rotatory cylinder containing the silicon is also heated and maintained at 300° C. The geared motor is turned on to spin the cylinder 60 to 80 rpm. The nitrogen feed is slowed down just enough to prevent air from entering the rotatory cylinder from the opened outlet. Hot chlorine gas is fed from a small cylinder at a rate of 2.5 slpm (standard liter per minute) for about 10 minutes to clean the silicon particles' surfaces by reacting away some silicon and metallic impurities which are mainly iron and aluminum. The reaction of silicon and chlorine produces mostly silicon tetrachloride which can be seen as a white smoke coming out at the outlet of the rotating cylinder. The white smoke consists of aerosol of hydrochloric acid and silica produced by the reaction of silicon tetrachloride vapor with moisture in the atmosphere. The white smoke and silicon tetrachloride vapor are safely disposed by scrubbing with a dilute solution of sodium hydroxide. After 10 minutes, the chlorine gas feed is increased to 8 slpm for 20 seconds. Then, the copper chloride aerosol smoking gun is fired by rapidly opening the ball valve to feed a puff of about 0.4 gram of the fine copper powder through the burner assembly and into the Pyrex glass combustion chamber containing the rapid flow of hot chlorine gas. A puff of white smoke is seen at the outlet immediately after the firing of the copper powder. The chlorine feed is maintained at 8 slpm for 10 seconds after the firing and then reduces to 1 slpm. The cylinder containing the silicon is let spinning for about 2 minutes to give sufficient time for the copper chloride aerosol to interact with the silicon particles. During these 2 minutes, another charge of about 0.4 gram copper powder is loaded under 8 psig of nitrogen pressure and is then ready to fire. At the end of the 2 minutes, the copper chloride aerosol smoking gun is again fired in the same manner as described above. The same procedure is repeated to fire the smoking gun for a total of 10 times. The flow of chlorine gas is shut off and replaced by nitrogen to flush out residual chlorosilane inside the rotatory cylinder. The geared motor is stopped. All the electric heaters are also shut off. A gentle flow of nitrogen is fed at the outlet end of the cylinder to keep the contents under nitrogen while the cylinder is removed from the heating tube and disconnected from the Pyrex glass combustion chamber. The resulting silicon/copper contact mass is cooled to room temperature and stored in a large bottle under an atmosphere of nitrogen. A sample of this contact mass is analyzed to give a copper content of 0.093% by weight. Thus, the 5 pounds of contact mass contains a total of 5×453.6×0.093%=2.1 grams of copper. The total amount of the −325 mesh copper powder used to produce the copper chloride aerosol is about 10×10.4=4 grams. The copper utilization efficiency is about 2.1×100×53%. In other words, only about 53% of the copper is picked up by the silicon particles in the form of copper chloride aerosol. This is mot likely due to the small size rotatory cylinder resulting in a relatively short resident time for the copper chloride aerosol inside the cylinder. In a large production size, rotatory calciner design, the volume of the rotating cylinder will be many times that of the small cylinder of the laboratory apparatus. In this case, the copper chloride aerosol is retained in contact with the silicon particles for a much longer period of time. One can expect the efficiency of copper utilization to significantly increase over the 53% achieved in this experiment.

EXAMPLE 9

The active silicon/copper contact mass prepared in EXAMPLE 8 is tested in the direct reaction with methyl chloride to make methylchlorosilanes in the same manner as described in EXAMPLE 6. Two hundred grams of the 50×150 mesh contact mass are thoroughly mixed with 0.2 gram zinc carbonate and 0.025 gram tin oxide in a bottle. The mixture is charged into the same laboratory glass fluidized bed reactor and reacted with methyl chloride in a similar manner as described in EXAMPLE 6. After several hours, the direct reaction reaches a steady state to give a fairly constant reaction rate, dimethyldichlorosilane yield and selectivity. The results set forth in TABLE 3 below are those of the average of three successive hours of reaction after the steady state.

TABLE 3

| Copper Content | % MeSiCl$_3$ | % Me$_2$SiCl$_2$ | % Residue | T/D Ratio | % Si Conv. per hour |
|---|---|---|---|---|---|
| 0.093% | 4.32 | 88.25 | 4.39 | 0.049 | 0.94 |

The results disclosed in TABLE 3 show that active silicon/copper contact mass prepared from the copper chloride aerosol generated by the combustion of copper metal in hot chlorine gas performs quite well in the direct reaction. The contact mass contains as little as 0.093% copper by still provides good yield and selectivity toward dimethyldichlorosilane in the direct reaction.

EXAMPLE 10

Another contact mass is prepared from the same 50×150 mesh metallurgical grade silicon by the same procedure and conditions set forth in EXAMPLE 8, except that more copper powder is used to build up a higher copper content in the contact mass. In this experiment, the copper chloride aerosol smoking gun is fired 20 times instead of 10 times as described in EXAMPLE 8. Analysis of a sample of the resulting contact mass shows the presence of 0.21% by weight of copper. Two hundred grams of this contact mass and 0.2 gram of zinc carbonate are thoroughly mixed and charged into the laboratory glass fluidized bed reactor. No tin oxide is added at this point. The purpose is to test the direct reaction in the absence as well as the presence of the tin promoter. The direct reaction with methyl chloride is carried out at 320° C. in the same manner as described in EXAMPLE 6. The results set forth in TABLE 4 below are those of the average of four successive hours of reaction after the steady state had been reached.

TABLE 4

| (no tin promoter added) | | | | | |
|---|---|---|---|---|---|
| Copper Content | % MeSiCl$_3$ | % Me$_2$SiCl$_2$ | % Residue | T/D Ratio | % Si Conv. per hour |
| 0.21% | 4.52 | 86.10 | 4.63 | 0.053 | 0.53 |

After the data in TABLE 4 has been collected, the direct reaction is continued with tin promoter added. Two grams of the contact mass, 0.05 gram zinc carbonate and 0.02 gram tin oxide are mixed and added along with the methyl chloride gas into the bottom of the fluidized bed reactor while the direct reaction is in progress. The direct reaction is monitored by measuring the reaction rate and the composition of the methylchlorosilane products. In every two hours, 2 grams of the contact mass, 0.05 gram zinc carbonate and 0.01 gram tin oxide are mixed and added into the fluidized bed reactor. After several hours, the direct reaction reaches a steady state to give a fairly constant reaction rate, dimethyldichlorosilane yield and selectivity. The results set forth in TABLE 5 are those of the average of four successive hours of reaction after the steady state has been reached.

TABLE 5

| (with tin promoter added) | | | | | |
|---|---|---|---|---|---|
| Copper Content | % MeSiCl$_3$ | % Me$_2$SiCl$_2$ | % Residue | T/D Ratio | % Si Conv. per hour |
| 0.21% | 3.26 | 88.54 | 4.87 | 0.037 | 1.4 |

Results in TABLE 5 show a large increase in the reaction rate of 1.4% Si conv./hr. with tin promoter added in comparison with the reaction rate at 0.53% Si conv./hr. in TABLE 4 with no tin promoter added. The effect of tin promoter to enhance the direct reaction was first disclosed by Radosavlyevich et al in a Serbian language article published in Glas. Hem. Drus. Beograd 30, 319 (1965). Radosavlyevich discloses that at 0.12% tin relative to copper, the reaction rate is observed to increase by 50%. However, there was no disclosure on the methylchlorosilane product distribution. The results disclosed in this instant invention are in qualitative agreement with the results disclosed by Radosavlyevich. Ward et al disclose in U.S. Pat. No. 4,500,724 and in an article entitled "Catalysis of the Rochow Direct Process" published in the Journal of Catalysis, 100, 240-249 (1986) the utilization of tin promoter to enhance the reaction rate and selectivity of the direct reaction. For example, Ward in TABLE 4, page 245 of the article published in the Journal of Catalysis discloses a selectivity of T/D ratio of 0.09 obtained from a contact mass consisting of 1.3 to 256 microns size silicon, 5% copper (from cuprous chloride) and 0.5% zinc in the direct reaction with methyl chloride with no tin added. When 0.005% tin is added to the same contact mass, Ward discloses in TABLE 4 of the article a large improvement of the selectivity in the direct reaction with a T/D ratio of 0.05. The data in TABLE 4 and in TABLE 5 of this invention show that the application of tin oxide promoter also significantly improves the selectivity from a T/D ratio of 0.053 to 0.037. These results are in fairly good agreement with those disclosed by Ward et al.

In the article published in the Journal of Catalysis, Ward also discloses the particle size of the cuprous chloride in the range of 2 to 5 microns. The contact mass used by Ward in the direct reaction contains 5% copper derived from this 2 to 5 microns cuprous chloride. In contrast, the contact mass disclosed in this invention for the direct reaction shown in TABLE 4 and TABLE 5 contains only 0.21% copper. Again, the extremely fine copper chloride aerosol with much smaller particle size 0.1 to 0.01 micron and smaller in comparison with the 2 to 5 microns size cuprous chloride used by Ward is the reason which makes this large reduction of copper requirement in the direct reaction possible.

In another example Halm discloses in U.S. Pat. No. 4,602,101 issued Jul. 22, 1986 and in U.S. Pat. No. 4,762,940 issued Aug. 9, 1988, respectively, a new phosphorous and a new arsenic promoter for the direct reaction. In both patents, Halm disclosed a contact mass basically composed of 6.1 parts of cuprous chloride powder and 100 parts of metallurgical grade silicon which consists of a maximum particle size of 70 microns with the majority 85% below 70 microns. To this contact mass, a variety of promoters including the new phosphorous and arsenic promoters are added in order to study the effects of these promoters in the direct reaction. The selectivity of the direct reaction cited in a large number of examples disclosed by Halm shows a low of 0.04 to a high of 0.21 with a majority in the 0.05 to 0.07 range. These selectivity values are comparable to the value of 0.053 in TABLE 4 and 0.037 in TABLE 5 of this invention. The 6.1 parts of cuprous chloride powder disclosed by Halm works out to be approximately 3.9% copper in the contact mass. In contrast, the contact mass used in this instant invention contains only 0.21% copper. Although Halm did not disclose the particle size of the cuprous chloride used in the contact mass, the much smaller copper chloride aerosol is most likely the reason for the much smaller amount of copper needed in the contact mass for a comparable performance in the direct reaction. A direct comparison of the reaction rate is not possible because of the large differences between the silicon particle size, 85% below 70 microns, used by Halm and the silicon particle size, 105 to 300 microns, used in TABLE 4 and in TABLE 5 of this invention. In conclusion, the examples cited above provide the testimony to prove the validity of the new methods disclosed in this instant invention to use a copper catalyst vapor and/or aerosol to prepare active silicon/copper contact mass for the direct reaction.

EXAMPLE 9

The fluidized bed reactor used to carry out the direct reaction for the production of methylchlorosilanes is itself a good mechanical mixing device. The laboratory glass fluidized bed reactor is modified with the capability to individually feed methyl chloride, nitrogen, pure chlorine and a mixture of 20% chlorine in nitrogen. An amount of 190 grams of 65×150 mesh, 210×105 microns, metallurgical grade silicon is charged into the fluidized bed reactor. Twenty grams of the same silicon are thoroughly mixed with 1.3 grams of a −325 mesh copper metal. The mixture is divided into 8 equal portions. The reactor containing the silicon is heated to 320° C. under nitrogen. Once the reactor reaches 320° C., a mixture of 20% chlorine and nitrogen is fed to gently fluidize the silicon mass bed. Liquid chlorosilane products which contain mostly silicon tetrachloride soon appear at the −40° C. condenser. The reaction continues for about 10 minutes to clean the silicon particles' surfaces by reacting away from some silicon and metallic impurities which consist mostly of iron and aluminum. One portion of the silicon/copper mixture is placed in a small glass funnel connected to the methyl chloride feed line through a glass stopcock. The funnel is pressurized with 6 psig of nitrogen. The 20% chlorine in nitrogen mixture is turned off and replaced by pure chlorine gas at about the same feed rate to the fluidizes silicon mass bed. About 15 seconds after the chlorine feed, the stopcock at the bottom of the funnel is opened. The nitrogen pressure forces the silicon/copper mixture into the flowing chlorine gas and is carried into the fluidized bed reactor. The pure chlorine feed is continued for 30 seconds. Then, it is replaced by the gaseous mixture containing 20% chlorine in nitrogen for two minutes to provide sufficient time to thoroughly mix the silicon/copper mass bed and to allow the chemical reaction to form the Cu-Si alloys on the silicon particles' surfaces. The same procedure is repeated seven times to charge all the 8 portions of the silicon/copper mixture into the fluidized bed reactor. The resulting contact mass is let cooled to room temperature under nitrogen. A sample of the contact mass is taken from the middle of the mass bed for copper analysis. The result of the analysis shows a 0.45% copper content in the contact mass. The contact mass bed in the fluidized bed reactor is re-heated to 320° C. Methyl chloride is fed to gently fluidize the contact mass bed. A mixture of 1 gram of the contact mass and 0.4 gram zinc carbonate is charged into the reactor at the start of the direct reaction. The contact mass is reactive right at the start of the direct reaction with no induction period observed. The direct reaction is carried out for several hours with periodic addition of 0.075 gram zinc carbonate promoter until a steady state is reached to give a fairly constant reaction rate, dimethyldichlorosilane yield and selectivity. The results set forth in TABLE 6 are those of the average of six hours of reaction after the steady state has been reached.

TABLE 6

| Copper Content | % $MeSiCl_3$ | % $Me_2SiCl_2$ | % Residue | T/D Ratio | % Si Conv. per hour |
|---|---|---|---|---|---|
| 0.45% | 4.51 | 91.10 | 1.87 | 0.05 | 1.3 |

The utilization of chlorine gas to activate a copper metal catalyst and silicon to make an active contact mass for the direct reaction in a fluidized bed reactor is unique and novel. It has never been disclosed in the prior art. This chlorine treatment method has certain advantages in the commercial production of methylchlorosilanes because the active silicon/copper contact mass can be prepared in the same fluidized bed reactor used for the direct reaction. For the silicone producers who practice the direct reaction, a spare reactor or an older reactor for the production of methylchlorosilanes may be modified to prepare the active contact mass by this chlorine treatment method. The results can be substantial savings in the costs of new production equipment.

The new methods of using copper catalyst vapor/aerosol to prepare active silicon/copper contact mass for the direct reaction set forth in this instant invention can be applied to promoters which are known in the prior art to enhance the direct reaction for the production of methylchlorosilanes. The most commonly used promoters are those of zinc (Zn), tin (Sn), antimony (Sb), arsenic (As) and phosphorous (P). Many volatile compounds of these elements are known and commercially available. For example, the chlorides (Cl) of these elements are quite volatile; $ZnCl_2$, b.p. 732° C.; $SnCl_2$, b.p. 623° C.; $SnCl_4$, b.p. 114° C.; $SbCl_3$, b.p. 223° C.; $AsCl_3$, b.p. 130° C. and $PCl_3$, b.p. 76° C. The promoter vapor/aerosol can be much more easily generated by simply heating these low boiling chlorides at a much lower temperature than that required for the cuprous chloride vapor/aerosol. The promoter vapor/aerosol can be applied to the same mechanical mixing devices set forth in this instant invention during the preparation of the active silicon/copper contact mass for the direct reaction to produce organohalosilanes.

Although the present invention has been described with reference to particular embodiments, it will be apparent to those skilled in the art that variations and modifications can be substituted therefor without departing from the principles and spirit of the invention.

I claim:

1. A method to prepare an active silicon/copper contact mass for the direct reaction of an organic halide with silicon to make organohalosilanes, said method comprising the steps of:
   treating particles of silicon with a copper catalyst vapor in a mechanical mixing device;
   mixing said silicon particles with said copper catalyst vapor;
   contacting said vapor with said particles; and
   forming active Cu-Si alloys on said particles to form said contact mass.

2. A method to prepare an active silicon/copper contact mass for the direct reaction of an organic halide with silicon to make organohalosilanes, said method comprising the steps of;
   treating particles of silicon with a copper catalyst aerosol in a mechanical mixing device;
   mixing said silicon particles with said copper catalyst aerosol;
   contacting said aerosol with said particles; and
   forming active Cu-Si alloys on said particles to form said contact mass.

3. The method of claim 1 or 2 wherein said copper catalyst is any volatile copper compound.

4. The method of claim 3 wherein said volatile copper compound is cuprous chloride.

5. The method of claim 3 further including generating said copper catalyst with a gaseous flow of an inert gas.

6. The method of claim 5 further including containing said generation in a container heated to a high temperature.

7. The method of claim 6 wherein said container is a combustion chamber; and
   further including reacting by an exothermic chemical reaction to a finely divided copper metal and a halogen gas within said chamber to produce said copper catalyst.

8. The method of claim 7 wherein said halogen gas is chlorine gas.

9. The method of claim 1 or 2 wherein said organic halide is a member of the group consisting of an alkyl chloride having 1-8 carbon atoms and aryl chloride.

10. The method of claim 9 wherein said alkyl chloride is methyl chloride and the aryl chloride is phenyl chloride.

11. The method of claim 1 or 2 wherein said silicon is of a grade containing more than 50%, but less than 100%, by weight of silicon.

12. The method of claim 1 further including preparing said contact mass using a promoter vapor in said treatment step.

13. The method of claim 2 further including preparing said contact mass using a promoter aerosol in said treatment step.

14. A method for preparing an active silicon/copper contact mass comprising:
   feeding a mixture of chlorine gas and finely divided copper metal into a fluidized bed of silicon at a temperature of approximately 260° C.

15. The method of claim 1 or 2 further including providing said copper catalyst in a particle size in the range of 0.01-0.1 micron.

16. The method of claim 1 or 2 wherein the particle size of said copper catalyst is less than 0.01 micron.

* * * * *